US005139475A

United States Patent [19]

Robicsek

[11] Patent Number: 5,139,475

[45] Date of Patent: Aug. 18, 1992

[54] MEDICAL APPLIANCE FOR TREATING VENOUS INSUFFICIENCY

[76] Inventor: Francis Robicsek, 1960 Randolph Rd., Charlotte, N.C. 28207-1199

[21] Appl. No.: 567,289

[22] Filed: Aug. 14, 1990

[51] Int. Cl.$^5$ .......................... A61F 5/00; A61B 19/00

[52] U.S. Cl. .......................................... 602/4; 602/13; 128/DIG. 20; 128/898

[58] Field of Search ....... 128/882, 87 R, 82, DIG. 20, 128/80 H, 89 R, 90, 91 R, 165, 166, 25 R, DIG. 25; 602/5, 3, 6, 13, 20, 21, 23, 27, 60, 61, 62, 63, 65

[56] References Cited

U.S. PATENT DOCUMENTS

| | | | |
|---|---|---|---|
| 746,338 | 12/1903 | Keen | 128/DIG. 20 |
| 2,493,878 | 1/1950 | Kirtz | 128/82 |
| 2,582,648 | 1/1952 | Mowbray | 128/82 |
| 2,694,395 | 11/1954 | Brown | 128/DIG. 20 |
| 3,083,708 | 4/1963 | Gottfried | 128/DIG. 20 |
| 3,164,152 | 1/1965 | Nicoll | 128/DIG. 20 |
| 3,186,404 | 6/1965 | Gardner | 128/DIG. 20 |
| 3,338,237 | 8/1967 | Sconce | 128/DIG. 20 |
| 3,351,055 | 11/1967 | Gottfried | 128/DIG. 20 |
| 3,785,374 | 1/1974 | Lipson | 128/DIG. 20 |
| 3,811,434 | 5/1974 | Jacobson | 128/DIG. 20 |
| 3,824,992 | 7/1974 | Nicholson | 128/DIG. 20 |
| 4,098,268 | 7/1978 | Scott | 128/DIG. 20 |

*Primary Examiner*—Michael Brown

*Attorney, Agent, or Firm*—Shefte, Pinckney & Sawyer

[57] ABSTRACT

A medical appliance worn about a patient's lower leg for treating venous insufficiency of the leg includes foot and leg portions having a hollow interior area extending therebetween for inflation into conformity with the patient's leg. When the patient is at rest, internal air pressure causes the stocking to function as an elastic stocking, but when the patient stands and walks, the force placed on the foot forces inflating air from the foot portion into the leg portion to increase the compressive action in the nature of a compression boot.

1 Claim, 2 Drawing Sheets

MEDICAL APPLIANCE FOR TREATING VENOUS INSUFFICIENCY

BACKGROUND OF THE INVENTION

The presently available most effective conservative management for venous insufficiency of the lower extremities, especially venous insufficiency associated with lymphedema, are elastic stockings and intermittent compression boots. Elastic stockings provide an appropriate support when the patient is standing or walking and intermittent compression boots literally "squeeze out" edematous fluids of the lower extremities thus improving circulation in both the venous as well as in the lymphatic systems.

SUMMARY OF THE INVENTION

It is an object of the present invention to provide a medical appliance which combines the advantages of elastic stockings and compression boots.

Briefly summarized, the medical appliance of the present invention is adapted for wearing on a patient's lower leg for treating venous insufficiency of the leg. The appliance has a leg portion for encircling the calf and ankle of the patient's leg and a foot portion for encircling the foot of the patient including an extent which underlies the foot. The appliance has a hollow interior area which is inflated by air when worn to cause the appliance to conform to the patient's leg. The hollow interior area extends from the underlying extent of the foot portion to the leg portion of the appliance. Thus, inflating air is distributed throughout the hollow interior area when the patient is seated or otherwise at rest so as not to exert any downward force through the leg, whereby the appliance functions in the nature of an elastic stocking. On the other hand, when the patient is standing, walking or otherwise exerting a downward force through the leg, inflating air is compressed within the hollow interior area out of and away from the foot portion, thereby causing the appliance to function as a compression boot.

In one embodiment, the appliance is a two-ply stocking worn about the foot and leg of the patient. In another embodiment, the appliance includes a two-ply stocking member worn about the leg and a boot member worn about the foot, with the stocking and boot members having respective communicating hollow interior areas.

DESCRIPTION OF THE PREFERRED EMBODIMENTS

Figure 1:
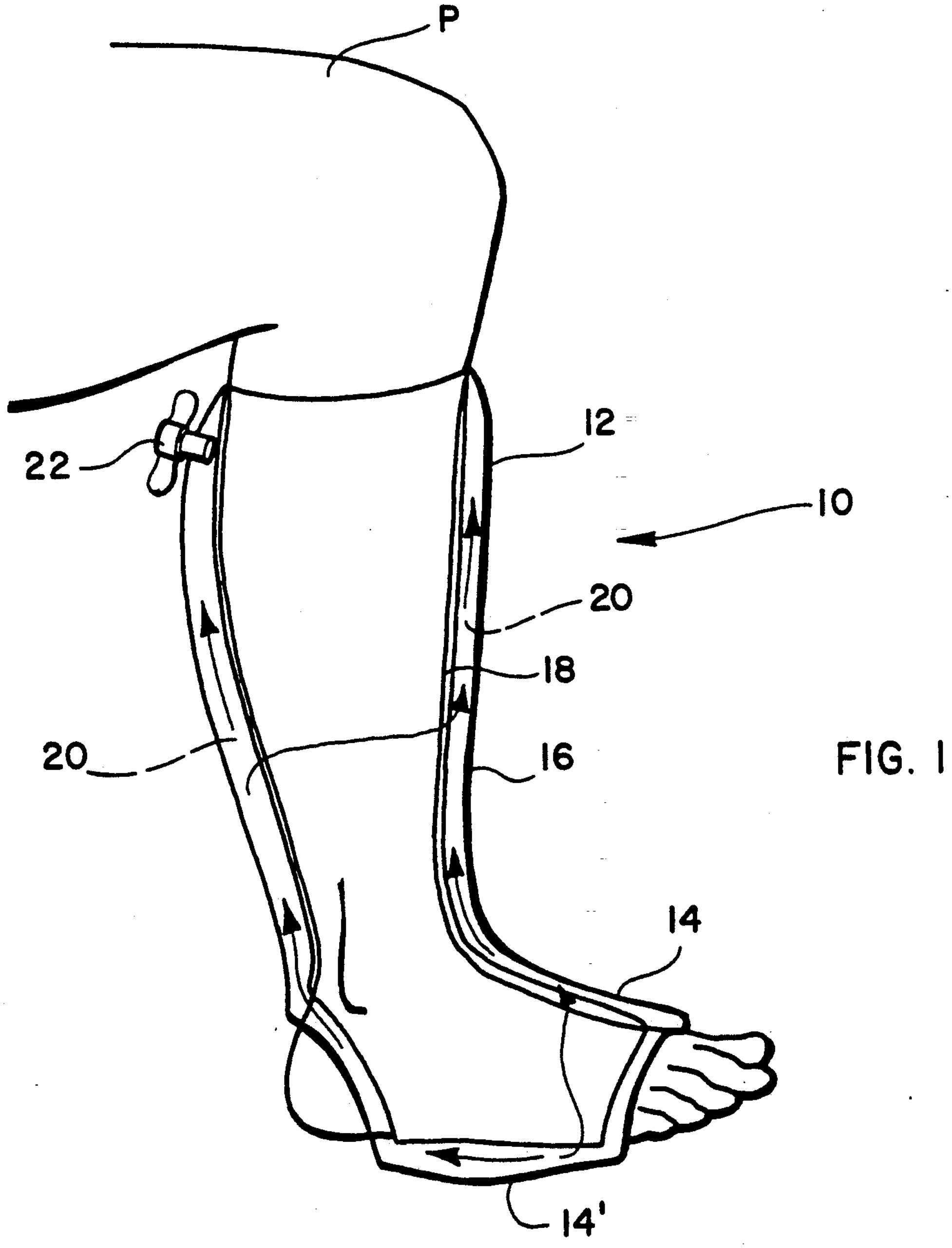
FIG. 1 is a schematic perspective view of a medical appliance according to one preferred embodiment of the present invention.

Referring now to the accompanying drawings and initially to FIG. 1, the medical appliance of the present invention is illustrated as embodied in a stocking 10 to be worn about the lower leg of a patient P. The stocking 10 is essentially tubular, including a leg portion 12 for encircling the calf and ankle of the patient's leg and a foot portion 14 for encircling the foot of the patient P, with a rearward opening for the patient's heel. The foot portion 14 includes a lower extent 14' directly underlying the ball and sole of the patient's foot. The stocking 10 has an outer layer 16 and an inner layer 18 extending the full length of the stocking 10 and joined together at the upper and lower annular extremities and about the heel opening of the stocking 10 to define therebetween a hollow interior area 20. A stopcock or other suitable valve device 22 is provided in the outer layer 16 for admitting and exhausting air into the hollow interior area 20 for selective inflation and deflation of the stocking 10.

In use, the stocking 10 is worn about the lower leg of the Patient P as illustrated in FIG. 1 and is inflated through the stopcock 22 with the patient's leg at rest, i.e., seated or elevated, to conform the stocking 10 to the patient's calf, ankle and foot with a degree of compressive pressure comparable to that exerted by conventional elastic stockings. Thus, while the patient is seated or otherwise at rest without the patient's weight placed on the leg or otherwise exerting a downward force through the leg, the inflating air is generally distributed throughout the interior area 20 causing the stocking 10 to function in the nature of a conventional elastic stocking. However, when the patient stands, walks or otherwise places weight on, or exerts a downward force through, the leg, the patient's foot compresses inflating air out of the extent of the foot portion underlying the patient's foot, forcing the air upwardly through the hollow interior area into the leg portion 12, thereby creating increased compressive pressure within the stocking 10 to cause it to function in the nature of a compression boot. In this manner, the stocking 10 continuously produces an intermittent "squeezing" action upon the calf of the patient while the patient is walking, while providing a continuous lesser degree of compression while the patient is at rest.

Figure 2:
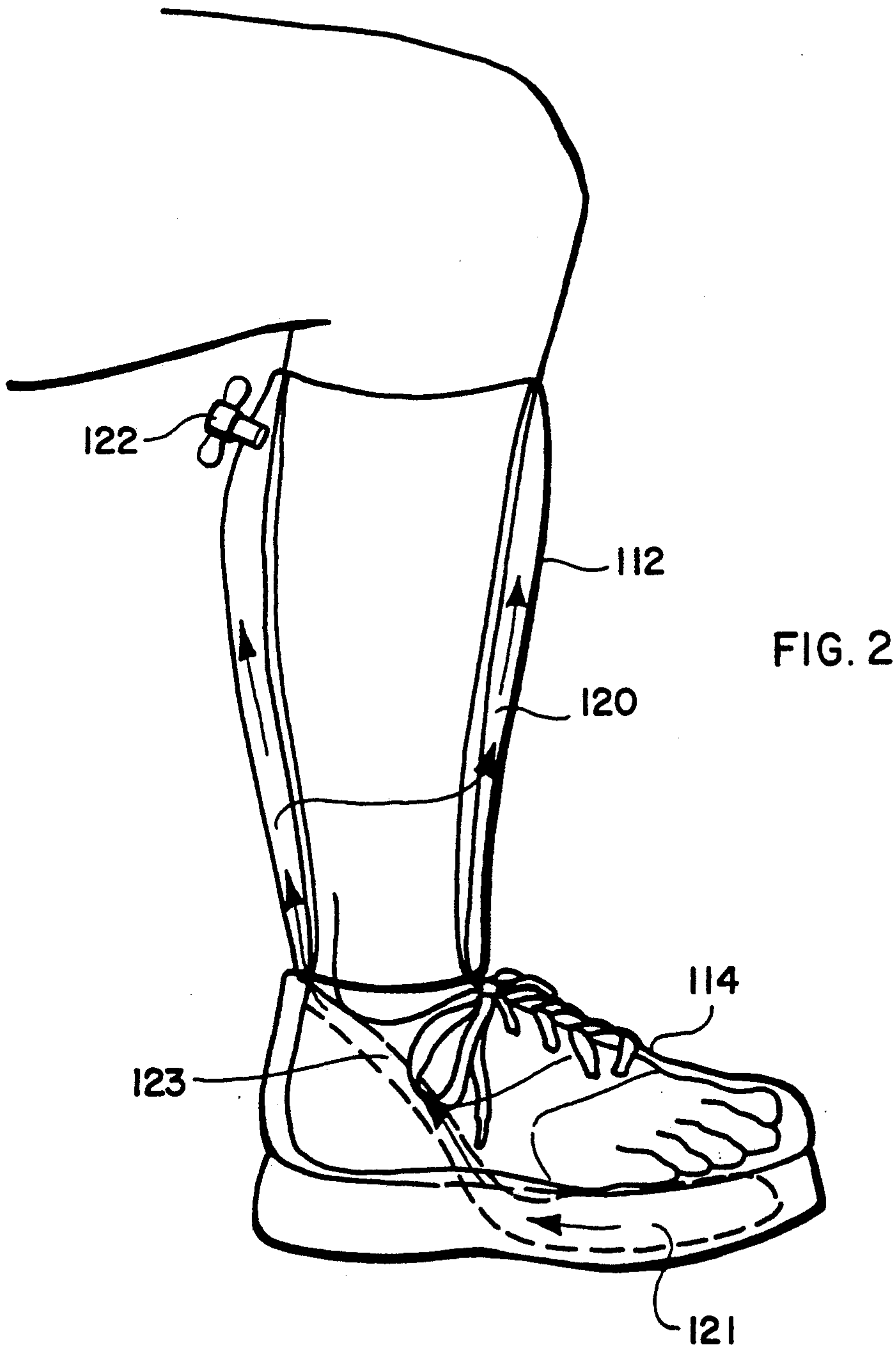
FIG. 2 is another schematic perspective view of a medical appliance according to a second preferred embodiment of the present invention.

FIG. 2 illustrates an alternative embodiment of medical appliance according to the present invention which provides an inflatable hollow two-ply stocking member 112 worn about the ankle and calf of the lower leg of a patient P and a boot member 114 having a hollow interior area 121 underlying the patient's foot. The stocking and boot members 112, 114 are connected together through a connecting air duct 123 with their respective hollow interior areas in communication. Thus, the hollow interior area 120 of the stocking member 112 and the hollow interior 121 of the boot member 114 are inflated and deflated together through a stopcock or valve 122. In turn, the appliance operates and functions in the same manner as described above for the stocking 10 when the patient is walking or at rest.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A method of treating venous insufficiency of a patient's leg comprising the steps of:

(a) providing a stocking having a leg portion for encircling the calf and ankle of the patient's leg and a foot portion for encircling the foot of the patient including an extent for underlying the foot, said stocking having a hollow interior area for inflation by air to conform said stocking to the patient's leg, said hollow interior area extending from said underlying extent of said foot portion to said leg portion;

(b) placing said stocking on the patient's lower leg;

(c) partially inflating said hollow interior area of said stocking; and (d) said patient wearing said partially inflated stocking on the patient's lower leg during normal activities, including sitting, standing and walking;

the inflating air being distributed throughout said hollow interior area when the patient is seated and otherwise not exerting downward force through the leg, causing said stocking to function as an elastic stocking, and the inflating air being compressed within said hollow interior area away from said foot portion when the patient is standing, walking and otherwise exerting downward force through the leg, causing said stocking to function as a compression boot.

* * * * *